US00PP13438P3

(12) United States Plant Patent
Yanagida

(10) Patent No.: US PP13,438 P3
(45) Date of Patent: Dec. 31, 2002

(54) HYBRID TEA ROSE PLANT NAMED 'KEIHAYANASA'

(75) Inventor: Yoshitaka Yanagida, Hakanagawa-Ken (JP)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/832,834

(22) Filed: Apr. 12, 2001

(65) Prior Publication Data

US 2002/0007503 P1 Jan. 17, 2002

(30) Foreign Application Priority Data

Jul. 16, 2000 (JP) ..... 12634

(51) Int. Cl.[7] ..... A01H 5/00
(52) U.S. Cl. ..... Plt./137
(58) Field of Search ..... Plt./137, 136, 130

*Primary Examiner*—Bruce R. Campell
*Assistant Examiner*—June Hwu
(74) *Attorney, Agent, or Firm*—Burns, Doane, Swecker & Mathis, LLP

(57) ABSTRACT

A new and distinct variety of Hybrid Tea rose plant is provided which abundantly forms attractive salmon pink blossoms. The blossoms commonly possess approximately 30 to 34 petals per bloom. The buds are large and are borne on straight erect stems. Attractive dark green semi-glossy foliage is formed. The new variety is particularly well suited for forming cut flowers under greenhouse growing conditions.

1 Drawing Sheet

BOTANICAL/COMMERCIAL CLASSIFICATION

*Rosa hybrida*/Hybrid Tea Rose Plant.

VARIETAL DENOMINATION cv. 'Keihayanasa'.

SUMMARY OF THE INVENTION

The new variety of *Rosa hybrida* Hybrid Tea rose plant was discovered during 1998 in Japan while growing among plants of the 'Febesa' variety (U.S. Plant Pat. No. 11,529). The new variety of the present invention accordingly is believed to be a naturally-occurring mutation of the 'Febesa' variety of unknown causation.

It was found that the new variety of Hybrid Tea rose plant of the present invention possesses the following combination of characteristics:

(a) Forms large elongated buds on straight stems,
(b) Forms in abundance attractive salmon pink blossoms,
(c) Forms attractive dark green semi-glossy foliage, and
(d) Is particularly well suited for the production of cut flowers under greenhouse growing conditions.

The new variety well meets the needs of the horticultural industry and can be used to advantage during the commercial production of cut flowers under greenhouse growing conditions.

The new variety was selected and preserved primarily because of its distinctive blossom coloration that differed from the parent 'Febesa' variety. More specifically, the 'Febesa' variety exhibits light pink blossoms whereas the new variety of the present invention forms blossoms that are salmon pink in coloration. In addition, the number of petals per blossom is different. More specifically, the 'Febesa' variety commonly forms approximately 20 to 24 petals per blossom on average whereas the new variety of the present invention commonly exhibits approximately 30 to 34 petals per blossom on average.

The new variety of the present invention can be distinguished from the 'Keihatakaho' variety (U.S. Plant patent application Ser. No. 09/832,840, filed concurrently herewith) that also is a mutation of the 'Febesa' variety. More specifically, the 'Keihatakaho' variety forms deep pink blossoms having approximately 50 petals blossom.

The new variety has been found to undergo asexual propagation by a number of routes, including budding, grafting, and the rooting of cuttings. Such asexual propagation by the above-mentioned methods as performed in France has shown that the characteristics of the new variety are strictly transmissible by such asexual propagation from one generation to another.

The new variety has been named the 'Keihayanasa' variety.

BRIEF DESCRIPTION OF THE PHOTOGRAPH

The accompanying photograph shows as nearly true as it is reasonably possible to make the same, in a color illustration of this character, typical specimens of the flower of the new variety wherein the flower is shown in various stages of opening. The depicted plant was being grown in a greenhouse at Chiba-Ken, Japan during May.

DETAILED DESCRIPTION

The chart used in the identification of the colors is The R.H.S. Colour Chart of The Royal Horticultural Society, London, England. The terminology which precedes reference to the chart has been added to indicate the corresponding color in more common terms. The description is based on two year-old specimens of the new variety during April while budded on *Rosa indica* understock and growing in greenhouses at Le Cannet des Maures, Var, France.

Class: Hybrid tea.

Plant:

*Height.*—When pruned to a height of 85 cm, floral stems having a length of approximately 50 to 80 cm commonly are produced at the end of the growing season.

*Habit.*—Erect.

Branches:

*Color.*—Young stems: Yellow-Green Group 146A, and bear tiny prickles. Adult wood: Green Group 137A, and bear some prickles.

*Thorns.*—Size: medium, and approximately 1 cm in length on average. Quantity: numerous. Color: Greyed-Orange Group 167A, and near Greyed-Orange Group 167D when young.

Leaves:

*Stipules.*—Approximately 0.5 cm in width on average, approximately 1.5 cm in length on average, near Yellow-Green Group 147D in coloration, adnate, pectinate and narrow.

*Petioles.*—Near Yellow-Green Group 147A to 147D, and somewhat glandular.

*Leaflets.*—Number: 3, 5 and 7 (most often). Shape: elliptic. Serration: regular. Texture: smooth and glabrous. General appearance: very dense, dark green and semi-glossy foliage. Color (young foliage): upper surface: near Yellow-Green Group 147A. under surface: near Yellow-Green Group 147B. Color (adult foliage): upper surface: near Green Group 139A. under surface: near Green Group 138A.

Inflorescence:

*Number of flowers.*—Usually one per stem.

*Peduncle.*—Strong, glandular, with a few prickles, near Green Group 138B in coloration, and the length is approximately 8.5 cm on average.

*Sepals.*—Tomentose on the upper surface and smooth on the under surface, approximately 3.5 cm in length on average, near Green Group 137D in coloration and with some extensions as illustrated in the photograph.

*Buds.*—Shape: elongated. Size: large. Length: approximately 5.5 cm on average.

*Flower.*—Shape: commonly with a high center. Diameter: approximately 9 cm on average. Color (when opening begins): upper surface: salmon pink, near Red Group 38A. under surface: salmon pink, near Red Group 38B. Color (when blooming): upper surface: salmon pink, near Red Group 38A. under surface: salmon pink, near Red Group 38B. Color (spot at petal base): upper surface: near Yellow Group 2C. under surface: near Yellow Group 2D. Fragrance: none. Lasting quality: long when cut and placed in a vase with the blossoms commonly lasting approximately 9 to 11 days. Petal shape: rounded apex with an obtuse base and reflexed edges. Petal size: approximately 4 cm in length and width on average during July. Petal number: approximately 30 to 34 on average. Petal drop: the petals commonly detach cleanly. Petaloids: none observed. Stamen number: approximately 106 on average. Anthers: ochre in coloration, near Yellow- Orange Group 18B and approximately 0.3 cm in size on average. Pollen: ochre in coloration. Filaments: near Yellow-Orange Group 16D in coloration, and approximately 1 cm in length on average. Pistil number: approximately 146 on average. Stigmas: near Yellow-Orange Group 18D in coloration, and approximately 0.1 cm in size on average. Styles: near Greyed-Purple Group 184C in coloration, and approximately 1 cm in length on average. Receptacle: near Green Group 138B in coloration, approximately 1 cm in size, smooth, and in longitudinal section in the shape of funnel. Hips: none observed to date.

Development:

*Vegetation.*—Very vigorous.

*Blooming.*—Very abundant.

*Resistance to diseases.*—Good, especially with respect to Powdery Mildew.

I claim:

1. A new and distinct variety of Hybrid Tea rose plant characterized by the following combination of characteristics:

(a) Forms large elongated buds on straight stems,
(b) Forms in abundance attractive salmon pink blossoms,
(c) Forms attractive dark green semi-glossy foliage, and
(d) Is particularly well suited for the production of cut flowers under greenhouse growing conditions;

substantially as herein shown and described.

* * * * *

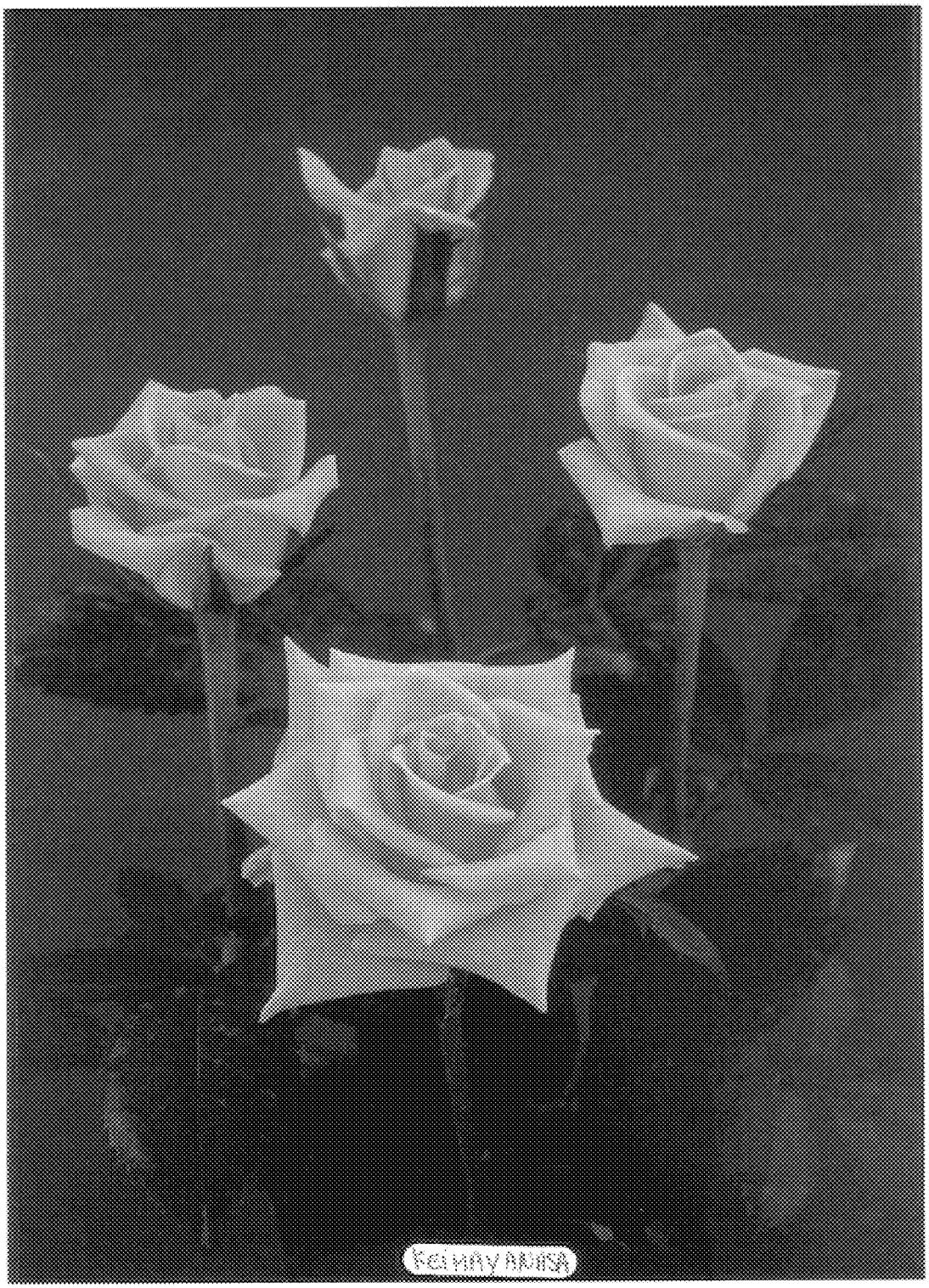
Sel MAY AMISA